United States Patent [19]

Kimura et al.

[11] Patent Number: 5,652,249
[45] Date of Patent: Jul. 29, 1997

[54] METHOD OF TREATING DEPRESSION

[75] Inventors: Kiyoshi Kimura, Osaka; Yojiro Ukai, Shiga, both of Japan

[73] Assignee: Nippon Shinyaku Co., Inc., Japan

[21] Appl. No.: 591,610

[22] PCT Filed: Jul. 27, 1994

[86] PCT No.: PCT/JP94/01235

§ 371 Date: Jan. 26, 1996

§ 102(e) Date: Jan. 26, 1996

[87] PCT Pub. No.: WO95/03801

PCT Pub. Date: Feb. 9, 1995

[30] Foreign Application Priority Data

Jul. 28, 1993 [JP] Japan ................ 5/207180

[51] Int. Cl.⁶ .................. A61K 31/445; A61K 31/495
[52] U.S. Cl. ........................... 514/326; 514/255
[58] Field of Search ................... 514/235.5, 326, 514/255

[56] References Cited

U.S. PATENT DOCUMENTS 5,102,882  4/1992  Kimura et al. ............... 514/235.5

*Primary Examiner*—Raymond Henley, III
*Attorney, Agent, or Firm*—Graham & James LLP

[57] ABSTRACT

The invention provides an antidepressant composition which comprises, as an active ingredient, a pyroglutamide derivative of the general formula [I]:

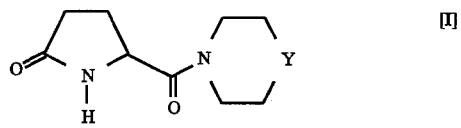

wherein Y is $CH_2$ or N—R (in which R is an alkoxycarbonyl group, a substituted or unsubstituted aralkyl group or a morpholinocarbonylalkyl group), or a pharmaceutically acceptable salt thereof.

The compound of the invention is useful in the prevention or treatment of depressive state or depression.

11 Claims, No Drawings

METHOD OF TREATING DEPRESSION

TECHNICAL FIELD

This is a 371 of PCT/JP94/01235 filed Jul. 27, 1994. This invention relates to an antidepressant composition.

BACKGROUND TECHNOLOGY

With the increasing complexity of the society, more and more people are succumbing to depression or presenting with depressive-like symptoms. The therapeutic regimen in use today is centered around tricyclic antidepressants (e.g. imipramine hydrochloride, desipramine hydrochloride, etc.). However, these drugs exert various side effects on the cardiovascular system, neuropsychological system, blood, liver, etc. and cannot be considered to be therapeutically satisfactory drugs. Accordingly there has been a standing demand for a new therapeutic agent.

Among the antidepressant drugs under development these days are 1) selective serotonin reuptake inhibitors, 2) specific monoamine reuptake inhibitors, and 3) $5\text{-HT}_{1A}$ receptor partial agonists.

Meanwhile, aniracetam which is a recently launched nootropic drug is expected to have ameliorative effects on emotional disturbances (anxiety, impatience, depressed mood) after brain infarct.

The cholinergic neurons in the central neurons system are deeply involved in learning and memory and reportedly many nootroic drugs have activity to stimulate neuronal system. On the other hand, it is known that anticholinergic drugs have inhibitory actions on both learning and memory.

Though neither the etiology of depression nor the detailed mechanisms of action of antidepressants have been elucidated as yet, many workers negate the idea that stimulation of the cholinergic nervous system elicits antidepressive effect. Rather, drugs having anticholinergic activity are known to produce antidepressant effects in animal experiments (F. Borsini and A. Meli: Psychopharmacology 94, 147–160, 1988).

The pyroglutamide derivatives to be utilized in accordance with the present invention have been investigated extensively by the present inventors as substances capable of remarkably alleviating learning and memory disabilities (Japanese Kokoku Tokkyo Koho Hei 04-55405; Japanese Kokai Tokkyo Koho Sho 62-252762).

DISCLOSURE OF THE INVENTION

It is an object of the present invention to provide a novel pharmaceutical composition differing in type from the known antidepressants and having a decreased potential for side effects.

The invention is thus directed to an antidepressant composition which comprises, as an active ingredient, a pyroglutamide derivative of the general formula [I]

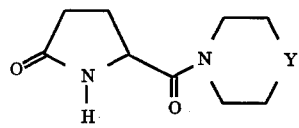

wherein Y is $CH_2$ or N—R (in which R is an alkoxycarbonyl group, a substituted or unsubstituted aralkyl group or a morpholinocarbonylalkyl group), or a pharmaceutically acceptable salt thereof.

It has now been found that such a known compound having alleviating effects on learning disabilities and disorders of memory has antidepressant activity which is quite irrelevant to said alleviating effects on learning disabilities and disorders of memory.

At present the mechanism by which the compound of the present invention acts as an antidepressant is unknown. Presumably, however, it is considered not to act on the serotonin or noradrenaline system.

In the following, the invention is described in more detail.

Referring to general formula [I], the alkoxy group is preferably a straight or branched lower alkoxy group containing 1 to 4 carbon atoms, such as methoxy, ethoxy, n-propoxy, isopropoxy, n-butoxy, isobutoxy, sec-butoxy or tert-butoxy. The aralkyl group preferably contains 7 to 11 carbon atoms and includes, among others, benzyl, phenethyl, phenylpropyl, phenylbutyl and phenylpentyl. The alkyl moiety of the aralkyl group may be branched. The alkyl as a substituent or substituents on the aryl moiety may be straight or branched and preferably contain 1 to 4 carbon atoms, methyl, ethyl, n-propyl, isopropyl, n-butyl, isobutyl, sec-butyl and tert-butyl being preferred examples. As the alkyl moiety of the morpholinocarbonylalkyl group, there may be mentioned those examples that are given above.

Among the compounds of general formula [I], that compound in which Y is $CH_2$ is particularly excellent in antidepressant activity and the D form thereof is more preferred.

When the compound [I] is used in the form of a salt, the salt may be a salt with an inorganic acid such as hydrochloric acid, sulfuric acid, nitric acid, phosphoric acid, hydrofluoric acid or hydrobromic acid, or with an organic acid such as formic acid, acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid or camphorsulfonic acid.

The compound to be used in accordance with the invention contains an asymmetric carbon atom, hence includes the D- and L-form optical isomers. It is to be noted that these optical isomers and mixtures thereof are all included within the scope of the present invention.

The following is a partial list of the compounds according to this invention.

1-(2-Pyrrolidone-5-carbonyl)piperidine (compound No. 1).

D-(+)-1-(2-Pyrrolidone-5-carbonyl)piperidine (compound No. 2).

4-Morpholinocarbonylmethyl-1-(2-pyrrolidone-5-carbonyl)piperazine (compound No. 3).

D-(+)-4-Morpholinocarbonylmethyl-1-(2-pyrralidone-5-carbonyl)piperazine (compound No. 4).

D-(+)-4-Morpholinocarbonylmethyl-1-(2-pyrrolidone-5-carbonyl)piperazine maleate (compound No. 5).

L-(−)-4-Morpholinocarbonylmethyl-1-(2-pyrrolidone-5-carbonyl)piperazine maleate (compound No. 6).

4-(2-Morpholinocarbonylethyl)-1-(2-pyrrolidone-5-carbonyl)piperazine (compound No. 7).

4-Ethoxycarbonyl-1-(2-pyrrolidone-5-carbonyl)piperazine (compound No. 8).

D-(+)-4-Ethoxycarbonyl-1-(2-pyrrolidone-5-carbonyl)piperazine (compound No. 9).

4-[3-(4-Methylphenyl)propyl]-1-(2-pyrrolidone-5-carbonyl)piperazine (compound No. 10).

4-(4-Methylbenzyl)-1-(2-pyrrolidone-5-carbonyl)piperazine (compound No. 11).

(D)-(+)-4-(4-Methylbenzyl)-1-(2-pyrrolidone-5-carbonyl)piperazine (compound No. 12).

The above is nothing but a partial listing of the compounds to be employed in the practice of the invention. All the compounds that are represented by the general formula given above can be used in practicing the present invention.

The compounds of formula [I] are per se known and can easily be prepared by the processes described in Japanese Kokai Tokkyo Koho Sho 62-252762 and Japanese Kokai Tokkyo Koho Sho 63-146857.

The compounds to be used in accordance with the invention have very low toxicity.

The antidepressant activity of the compound of this invention can be demonstrated by the following forced swimming and learned helplessness tests in rats. Particularly the forced swimming test has been used most widely in the evaluation of antidepressant drugs in animals. Reportedly the immobility time-shortening activity of an antidepressant drug as assayed by this test is highly correlated with the clinical efficacy of the drug in man (F. Borsini and A. Meli, 1988).

Experimental

1. Rat forced swimming test

Five-week old male Wistar rats were used. A cylindrical vessel measuring 18 cm in diameter and 40 cm deep was filled with 25° C. of water to the level of 17 cm from the bottom, and the rat was forced to swim in the water for 15 minutes (Session I). After 24 hours, the rat was put again in the vessel for 5 minutes and the duration of time the rat remained motionless without swimming was determined (Session II). The drug was orally administered twice, viz. at completion of Session I and 1 hr before the start of Session II. The drug was suspended in 0.5% methylcellulose (MC) solution for the administration. The control group was orally given the same volume of 0.5% MC solution. Compound No. 2 was used as the test drug. As reference drugs, desipramine, which is a representative antidepressant, and aniracetam and idebenone, both of which are enhancers of cerebral circulation and metabolism, were used. The statistical significance of between groups differences was analyzed by Dunnett's test. The results are shown in Table 1–Table 4.

TABLE 1

Effect of the test compound on the immobility time in the forced swimming test in rats

|  |  | N | Immobility Time (sec) (mean ± S.E.) |
|---|---|---|---|
| Control |  | 10 | 180.8 ± 10.2 |
| Comod. No. 2 | 0.3 mg/kg | 10 | 153.0 ± 17.2 |
|  | 1 | 10 | 119.4 ± 11.0* |
|  | 3 | 10 | 82.2 ± 18.1* |
|  | 10 | 10 | 93.7 ± 13.4* |
|  | 30 | 10 | 61.3 ± 8.5* |
|  | 100 | 10 | 53.8 ± 12.6* |

(*p < 0.01)

TABLE 2

Effect of despramine on the immobility time in the forced swimming test in rats

|  |  | N | Immobility Time (sec) (mean ± S.E.) |
|---|---|---|---|
| Control |  | 10 | 166.0 ± 17.5 |
| desipramine | 1 mg/kg | 10 | 134.2 ± 20.8 |
|  | 3 | 10 | 83.2 ± 16.1* |
|  | 10 | 10 | 54.7 ± 15.8* |
|  | 30 | 10 | 34.8 ± 12.2* |
|  | 50 | 10 | 41.8 ± 9.8* |

(*p < 0.01)

TABLE 3

Effect of aniracetam on the immobility time in the forced swimming test in rats

|  |  | N | Immobility Time (sec) (mean ± S.E.) |
|---|---|---|---|
| Control |  | 10 | 166.2 ± 16.7 |
| aniracetam | 10 mg/kg | 10 | 168.9 ± 18.0 |
|  | 30 | 10 | 162.6 ± 14.5 |
|  | 100 | 10 | 175.6 ± 13.8 |

TABLE 4

Effect of idebenone on the immobility time in the forced swimming test in rats

|  |  | N | Immobility Time (sec) (mean ± S.E.) |
|---|---|---|---|
| Control |  | 10 | 178.4 ± 20.5 |
| idebenone | 30 mg/kg | 10 | 178.2 ± 17.6 |
|  | 100 | 10 | 154.4 ± 17.4 |
|  | 300 | 10 | 180.9 ± 13.9 |

The compound of this invention shortened the immobility time significantly and dose dependently at 1 mg/kg and higher doses. The antidepressant desipramine shortened the immobility time significantly and dose dependently at 3 mg/kg and higher doses. In contrast, the nootropic aniracetam and idebenone did not influence the immobility time at 10–100 mg/kg and 30–300 mg/kg, respectively.

2. Rat learned helplessness test

The rat was orally administered with the drug once daily for 10 consecutive days. On days 8–10 of administration, the rat was placed in a shuttle box in which it received 100 unescapable electroconvulsive shocks (ECS) daily. The day after the last ECS session, the active avoidance task was given 40 times and the number of failures to escape was recorded. Compound No. 2 was used as the test drug. As a reference drug, desipramine was used. The results are shown in Table 5.

TABLE 5

Effect of test compounds on the learned helplessness in rats

|  |  | N | No. of escape failures (mean ± S.E.) |
|---|---|---|---|
| no ECS Group |  | 20 | 0.40 ± 0.18 |
| ECS Group |  |  |  |
| Control |  | 20 | 33.65 ± 1.39 |
| Compd. No. 2 | 1 mg/kg | 10 | 20.20 ± 4.89 |
|  | 3 mg/kg | 10 | 13.60 ± 4.15 |
|  | 10 mg/kg | 10 | 0.90 ± 0.69* |
| desipramine | 1 mg/kg | 10 | 32.10 ± 2.66 |
|  | 3 mg/kg | 10 | 19.00 ± 5.65 |
|  | 10 mg/kg | 10 | 0.60 ± 0.27* |

(*p < 0.01)

The unescapable ECS increased the number of escape failures in the task session (learned helplessness). Both the compound of this invention and desipramine showed significant inhibitory effects on this failure to escape at 10 mg/kg.

From the effectiveness of the compound of this invention as demonstrated by the above forced swimming and learned helplessness tests which are representative methods for the evaluation of antidepressive activity, it is clear that the compound of this invention has anti-depressant or mood elevating activity.

3. Acute toxicity testing (1) Groups of five male ddy-strain mice aged 6–7 weeks were used. The animals were fasted for 16–18 hours (from the previous day) and then orally given the test compound. The $LD_{50}$ values were calculated by the probit method based on the mortality observed within the succeeding period of 2 weeks.

For compound No. 2, the $LD_{50}$ value was found to be 4,162 mg/kg.

(2) Groups of five male SD-strain rats weighing 280–360 g were used. The animals were fasted for 16–18 hours (from the previous day) and then orally given the test compound. The $LD_{50}$ values were calculated by the probit method based on the mortality observed within the succeeding two-week period.

For compound No. 2, the $LD_{50}$ value was estimated at not less than 5,000 mg/kg.

Thus, it was found that the compound of the present invention is extremely low in toxicity.

The compound of the invention can be administered to animals including human either as it is or in the form of a pharmaceutical composition containing 0.1 to 99.5%, preferably 0.5 to 90%, of the compound and the balance of a pharmaceutically acceptable nontoxic and inert carrier.

The carrier may be at least one member of solid, semisolid or liquid diluents, fillers and other pharmaceutical auxiliary agents. The pharmaceutical composition is preferably administered in unit dosage forms. The pharmaceutical composition of the present invention can be administered orally, into the tissue, locally (e.g. transdermally) or rectally. Of course, the dosage form suitable for each route of administration should be selected. For example, oral administration is particularly preferred.

The dosage as an antidepressant is preferably adjusted in consideration of the patient's characteristics such as age and body weight, route of administration, nature and severity of disease and so on. Usually, however, the daily dosage as the active compound for human adults is 1 mg–5 g/man/day, preferably 150 mg–3 g/man/day for oral administration. Depending on cases, a lower dosage may suffice or a higher dosage may be necessary. The daily dosage may be administered in a few divided doses.

Oral administration can be carried out using a solid or liquid unit dosage form such as a neat powder, powder, tablet, dragee, capsule, granule, suspension, solution, syrup, drop, or sublingual tablet.

The neat powder can be prepared by comminuting the active compound to size. The powder can be manufactured by pulverizing the active compound to size and blending the resulting powder with similar powders of one or more pharmaceutical carriers such as edible carbohydrates, e.g. starch, mannitol and so on. If necessary, flavorants or corrigents, preservatives, dispersing agents, colorants, perfumes, etc. can be incorporated in the composition.

Capsules can be manufactured by preparing neat or formulated powders in the above manner or granules in the manner described hereinafter for tablets and, then, filling gelatin or other capsule shells with the powders or granules. Prior to the filling operation, a lubricant or fluidizing agent such as colloidal silica, talc, magnesium stearate, calcium stearate or solid polyethylene glycol can be added, each in finely divided state, to said granules. An improvement in effect of the drug administered may be obtained by adding a disintegrator or solubilizer such as carboxymethylcellulose, carboxymethylcellulose calcium, low-substituted hydroxypropylcellulose, crosscarmelose sodium, carboxymethylstarch sodium, calcium carbonate or sodium carbonate.

Soft-capsules can be manufactured by dispersing a powder of the compound of the invention in a vegetable oil, polyethylene glycol, glycerin or a surfactant and entrapping the dispersion in a gelatin sheet shells. Tablets can be manufactured by preparing a powdery composition with use of an excipient, making it into granules or slags, adding a disintegrator and/or lubricant thereto and compression-molding the whole composition. The powdery composition mentioned above may be a mixture of a finely divided powder of the compound of the invention and a diluent or base such as mentioned above, optionally supplemented with a binder (e.g. sodium carboxymethylcellulose, hydroxypropylcellulose, methylcellulose, hydroxypropylmethylcellulose, gelatin, polyvinylpyrrolidone, polyvinyl alcohol, etc.), a dissolution retardant (e.g. paraffin, wax, hydrogenated castor oil, etc.), a reabsorption agent (e.g. quaternary ammonium salts) and an adsorbent (e.g. bentonite, kaolin, dicalcium phosphate, etc.). The powdery composition can be granulated by wetting it with a binder such as a syrup, starch paste, gum arabic, a cellulose or polymer solution, followed by forced passage through a sieve. Instead of such a granulation process, the composition may first be tableted and the resulting slags of crude form are crushed to give granules.

To the granules which are manufactured in the above manner, an appropriate lubricant such as stearic acid, stearates, talc or mineral oil can be added for preventing the interadhesion of individual granules. The thus-lubricated composition is then compression-molded.

The uncoated tablets thus obtained can be film-coated or sugar-coated.

Instead of being processed through said granulation and slagging steps, the drug may be admixed with a free-flowing inert carrier and directly compression-molded. It is also possible to utilize a transparent or translucent protective coating comprising a hermetically sealing shellac film, and in lieu of, or on top of, said shellac film, a sugar or polymer coat and even a polished wax coat may be applied.

Other oral dosage forms such as solutions, syrups and elixers can also be provided in unit dosage forms so that the drug may be contained in constant quantities. Syrups can be manufactured by dissolving the compound in an appropriate flavored aqueous medium, while elixirs can be manufactured using a nontoxic alcoholic vehicle. Suspensions can be formulated by dispersing the compound in a nontoxic vehicle. Solubilizers and emulsifiers (e.g. ethoxylated isostearyl alcohol, polyoxyethylene sorbitol ester), preservatives, flavorants (e.g. peppermint oil, saccharin) and other agents can also be added, where necessary.

If necessary, such a unit dosage form for oral administration may be microencapsulated. Such a formulation can be coated or embedded in a polymer, wax or the like to insure a sustained action or controlled release.

Parenteral administration can be carried out using a liquid unit dosage form, e.g. a solution or a suspension, which has been prepared for subcutaneous, intramuscular or intravenous administration. Such dosage form can be manufactured by suspending or dissolving a predetermined amount of the compound in an injectable nontoxic liquid vehicle such as an aqueous or oily medium and sterilizing the resulting suspension or solution. It is also possible to put the compound in predetermined portions into vials and then sterilize the vials together with the contents and tightly close the vials. For dissolution or mixing just prior to use, the vials containing the active ingredient in powder or lyophilized form may be accompanied each by a supplementary vial containing a liquid vehicle. For isotonizing such an injectable preparation, a nontoxic salt or salt solution can be added. Furthermore, a stabilizer, a preservative, an emulsifier and/ or the like may be used additionally.

Rectal administration can be carried out using a suppository. Such suppositories can be manufactured by mixing the compound with a low-melting water-soluble or insoluble solid base such as polyethylene glycol, cacao butter, a higher fatty acid ester (e.g. myristyl palmitate) or a mixture of these.

BEST MODE FOR CARRYING OUT THE INVENTION

The following formulation examples are further illustrative of the present invention.

Formulation Example 1

The compound No. 2 is dissolved in physiological saline to give a 5% (weight/volume) solution. The solution was passed through a membrane filter and then distributed in 1-ml, 2-ml, 5-ml, 10-ml or 20-ml portions into appropriate ampules, followed by sealing and autoclaving to give injectable solution.

Formulation Example 2

Hard capsules are produced in the conventional manner, each comprising 500 mg of the compound No. 2, 124.0 mg of lactose, 1.3 mg of hydrated silicon dioxide, 12.8 mg of polyvinyl alcohol and 1.9 mg of magnesium stearate.

Formulation Example 3

Tablets are produced in the conventional manner, each comprising 250 mg of the compound No. 2, 181.2 mg of lactose, 77.6 mg of starch, 40.0 mg of crystalline cellulose, 17.1 mg of methylcellulose, 2.9 mg of hydrated silicon dioxide and 1.2 mg of magnesium stearate.

EFFECTS OF THE INVENTION

The compounds to be used in accordance with the present invention have potent antidepressant or mood elevating activity and have low toxicity. Therefore, they are useful in the treatment or prevention of psychotropic diseases such as depressive state or depression-like symptoms, depression, etc. and in improving the state of patients with cerebrovascular disorder or with senile dementia who present decreased spontaneity.

We claim:

1. A method for the treatment of depression in an animal suffering from depression, which comprises administering to the sufferer an antidepressive effective amount of a compound of the formula:

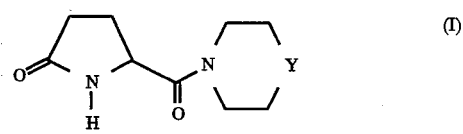

wherein Y is $CH_2$ or N—R, in which R is alkoxycarbonyl, substituted or unsubstituted aralkyl or morpholinocarbonylalkyl, or a pharmaceutically acceptable salt thereof.

2. The method according to claim 1, wherein said compound or salt has the D configuration.

3. The method according to claim 4, wherein Y is $CH_2$.

4. The method according to claim 3, wherein said compound or salt has the D configuration.

5. The method according to claim 1, wherein said compound is 1-(2-pyrrolidone-5-carbonyl)piperidine or D-(+)-1-(2-pyrrolidone-5-carbonyl)piperidine.

6. The method according to claim 1, wherein said compound is D-(+)-1-(2-pyrrolidone-5-carbonyl)piperidine.

7. The method according to claim 4, wherein Y is N—R, in which R is alkoxycarbonyl wherein the alkoxy moiety is $C_1$–$C_4$ alkoxy; aralkyl of 7 to 11 carbon atoms, wherein the aryl moiety is unsubstituted or substituted by $C_1$–$C_4$ alkyl; or morpholinocarbonylalkyl, wherein the alkyl moiety is $C_1$–$C_4$ alkyl.

8. The method according to claim 7, wherein R is morpholinocarbonylmethyl, morpholinocarbonylethyl, ethoxycarbonyl, (methylphenyl)propyl, or methylbenzyl.

9. The method according to claim 7, wherein said compound or salt has the D configuration.

10. The method according to claim 8, wherein said compound or salt has the D configuration.

11. The method according to claim 1, wherein said animal suffering from depression is a human suffering from depression.

* * * * *